(12) United States Patent
Amano et al.

(10) Patent No.: US 8,702,664 B2
(45) Date of Patent: Apr. 22, 2014

(54) TRANSDERMAL PREPARATION

(75) Inventors: Satoshi Amano, Tsukuba (JP);
Tomohiro Shinoda, Tsukuba (JP);
Natsumi Kase, Tsukuba (JP); Keita Mori, Tosu (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 0 days.

(21) Appl. No.: 13/201,999

(22) PCT Filed: Feb. 9, 2010

(86) PCT No.: PCT/JP2010/051853
§ 371 (c)(1),
(2), (4) Date: Oct. 19, 2011

(87) PCT Pub. No.: WO2010/095537
PCT Pub. Date: Aug. 26, 2010

(65) Prior Publication Data
US 2012/0029446 A1 Feb. 2, 2012

(30) Foreign Application Priority Data
Feb. 18, 2009 (JP) ................. P2009-035218

(51) Int. Cl.
*A61M 35/00* (2006.01)

(52) U.S. Cl.
USPC ............. 604/304; 604/19; 604/289; 424/443; 424/448; 424/449

(58) Field of Classification Search
None
See application file for complete search history.

(56) References Cited

U.S. PATENT DOCUMENTS

| | | | | |
|---|---|---|---|---|
| 4,588,580 A | * | 5/1986 | Gale et al. | 424/449 |
| 4,737,559 A | * | 4/1988 | Kellen et al. | 526/291 |
| 4,837,027 A | * | 6/1989 | Lee et al. | 424/449 |
| 4,908,027 A | * | 3/1990 | Enscore et al. | 604/890.1 |
| 5,217,718 A | * | 6/1993 | Colley et al. | 424/449 |
| 5,296,222 A | | 3/1994 | Petersen et al. | |
| 6,914,169 B1 | * | 7/2005 | Oota et al. | 602/58 |
| 2001/0038861 A1 | | 11/2001 | Hsu et al. | |

(Continued)

FOREIGN PATENT DOCUMENTS

| CN | 101626761 A | 1/2010 |
|---|---|---|
| DE | 19834505 | 2/2000 |

(Continued)

OTHER PUBLICATIONS

English Translation of the International Preliminary Report on Patentability; 8 pages; issued on Sep. 13, 2011.

(Continued)

*Primary Examiner* — Tan-Uyen T. Ho
*Assistant Examiner* — Eric Bryant
(74) *Attorney, Agent, or Firm* — Nath, Goldberg & Meyer; Sheldon M. McGee

(57) ABSTRACT

By providing a non-liquid drug reservoir layer 2 having first and second principal surfaces and containing a drug and a polymer that is to be a base, a drug permeation layer 4 disposed at the first principal surface side of the drug reservoir layer 2 and being lower in permeability of the drug than the drug reservoir layer 2, and a first backing 3 with a bending resistance of 10 to 80 mm that is formed so as to cover a side surface of the drug reservoir layer, skin irritation can be reduced.

14 Claims, 13 Drawing Sheets

(56) References Cited

U.S. PATENT DOCUMENTS

| | | |
|---|---|---|
| 2002/0034554 A1 | 3/2002 | Hsu et al. |
| 2003/0138479 A1* | 7/2003 | Mizota et al. ............... 424/443 |
| 2008/0292685 A1* | 11/2008 | Wang et al. ................. 424/449 |

FOREIGN PATENT DOCUMENTS

| | | | |
|---|---|---|---|
| JP | 62-169723 A | 7/1987 | |
| JP | 8-10340 A | 1/1996 | |
| JP | 2002-360626 A | 12/2002 | |
| JP | 2003-104875 A | 4/2003 | |
| JP | 2003104875 * | 4/2003 | ............ A61K 31/21 |
| JP | 2003-313122 A | 11/2003 | |
| JP | 2005-192672 A | 7/2005 | |
| JP | 2007-99759 A | 4/2007 | |
| JP | 2008-247899 A | 10/2008 | |
| JP | 4493332 B2 | 6/2010 | |
| WO | 9009809 | 9/1990 | |
| WO | 97/06847 A1 | 2/1997 | |
| WO | 9801111 | 1/1998 | |
| WO | 2005/072669 A1 | 8/2005 | |
| WO | WO2007069661 * | 6/2007 | ........... A61K 31/138 |
| WO | 2007/099966 A1 | 9/2007 | |

OTHER PUBLICATIONS

International Search Report; 3 pages; completed on Apr. 6, 2010; mailed on Apr. 20, 2010.

Search Report for European Patent Application No. 10743664.4 mailed on Jul. 19, 2013.

Chinese Office Action, CN Patent Application No. 201080007994.X, dated Dec. 5, 2012, five (5) pages.

* cited by examiner

TRANSDERMAL PREPARATION

This is a National Phase Application filed under 35 U.S.C. §371 as a national stage of PCT/JP2010/051853, filed on Feb. 9, 2010, an application claiming the benefit under 35 U.S.C. §119 of Japanese Application No. P2009-035218, filed on Feb. 18, 2009, the content of each of which is hereby incorporated by reference in its entirety.

TECHNICAL FIELD

The present invention relates to a transdermal preparation that is reduced in skin irritation.

BACKGROUND ART

Bisoprolol, which is a highly selective blocker (β blocker) of a sympathetic β1 receptor, is used for improvement of essential hypertension, angina or arrhythmia. For example, a fumarate thereof is administered orally in pill form. However in the case of oral administration, there are such disadvantages as a lack of persistence of effect, a higher than necessary blood concentration being seen temporarily after administration, side-effects occurring readily, etc. A practical transdermal preparation for improving on this situation is thus desired.

Bisoprolol-containing patches are described, for example, in Patent Literatures 1 to 4. In Patent Literature 1, a matrix type preparation containing a rubber-based adhesive is described and it is described that bisoprolol is skin irritating. In Patent Literature 2, a matrix type preparation (laminate type preparation) containing an acrylic adhesive is described. Also in Patent Literature 3, it is described that skin irritation can be reduced by controlling a dermal absorption rate of bisoprolol to be no more than a fixed value. However, with the preparation described in Patent Literature 3, a concentration of bisoprolol in an adhesive layer is low, it is premised that the preparation is to be re-attached each day, and actual use is thus cumbersome in consideration of the trouble of having to re-attach the preparation frequently.

Patent Literature 4 describes a laminate type preparation, which, as a transdermal preparation capable of transdermally administering bisoprolol over a long term with stability, includes a backing, a drug reservoir layer containing bisoprolol and an acrylic adhesive, and a skin adhesion inhibiting layer containing a styrene-isoprene-styrene block copolymer. With the laminate type preparation disclosed in Patent Literature 4, bisoprolol is contained at a high concentration in the drug reservoir layer and is made to be transdermally absorbed in a slowly released manner through a skin adhesion layer, thereby enabling a fixed amount of bisoprolol to be administered with stability over a long term (for example, 3 to 10 days), and a skin attachment property is also good.

CITATION LIST

Patent Literature

Patent Literature 1: Japanese Published Unexamined Patent Application No. 2007-99759
Patent Literature 2: Japanese Published Unexamined Patent Application No. 2003-31322
Patent Literature 3: Japanese Published Unexamined Patent Application No. 2008-247899
Patent Literature 4: WO 2007/99966 Publication

SUMMARY OF INVENTION

Technical Problem

However, with the transdermal preparation described in Patent Literature 3, the concentration of bisoprolol in the adhesive layer is controlled to be low to reduce skin irritation and thus to provide an arrangement for stable, long-term administration, an area of the preparation or a thickness of the drug reservoir layer must be increased. This is unfavorable as it leads to degradation of feeling of use and increase of cost.

Meanwhile, with the laminate type preparation described in Patent Literature 4, although skin irritation is alleviated while bisoprolol is contained at a high concentration, there are cases where strong skin irritation is seen at a peripheral portion of the preparation. For example, a liquid drug, such as bisoprolol in free form, is contained at a high concentration in the drug reservoir layer so that a cold flow occurs readily due to a plasticizing action, and there are thus cases where the preparation is attached with a side surface of the drug reservoir layer being in a so-called drooped state and cases where the drug reservoir layer becomes exposed due to movement of a patient, etc., and contacts the skin.

The present invention has been made to resolve such technical issues and an object thereof is to provide, in a transdermal preparation containing a drug that is strongly irritating to skin, a transdermal preparation that is capable of reliably reducing skin irritation by a simple arrangement.

Solution to Problem

That is, a transdermal preparation, which is one embodiment of the present invention, includes a non-liquid drug reservoir layer having first and second principal surfaces and containing a drug and a polymer that is to be a base, a drug permeation layer disposed at the first principal surface side of the drug reservoir layer and being lower in permeability of the drug than the drug reservoir layer, and a first backing with a bending resistance of 10 to 80 mm that is formed so as to cover a side surface of the drug reservoir layer.

With the transdermal preparation, which is one embodiment of the present invention, the drug permeation layer that is lower in permeability of the drug than the drug reservoir layer is disposed at the first principal surface side of the drug reservoir layer and thus transdermal absorption in a slowly releasing manner via the drug permeation layer can be achieved without letting the drug reservoir layer contact skin directly. Also, the first backing with the bending resistance of 10 to 80 mm is formed so as to cover the side surface of the drug reservoir layer and direct contact of the side surface of the drug reservoir layer with skin can thus be avoided. Skin irritation can thus be reduced.

Here, the transdermal preparation may include a second backing formed so as to cover the second principal surface side of the drug reservoir layer. By this arrangement, contact of the drug reservoir layer with skin can be avoided reliably.

Also, the second backing may be formed integral to the first backing. By this arrangement, manufacture can be facilitated. As the first backing, a polyethylene terephthalate film or a sheet made of a laminate of polyethylene terephthalate and a nonwoven fabric, etc. is used. By this arrangement, both reduction of skin irritation and drug impermeability can be realized at the same time.

Also, the drug permeation layer may have a wider area than the drug reservoir layer. By this arrangement, the first backing that covers the drug reservoir layer can be fixed reliably. Also, the drug permeation layer may have an adhesive property.

Also, the drug permeation layer may have a one-second creep compliance greater than $1\times10^{-6}$ cm$^2$/dyne in a range of 30 to 40° C. By this arrangement, the drug permeation layer can be made to function as a skin adhesion layer as well.

Also, the drug permeation layer may contain a rubber-based polymer. Also, the rubber-based polymer may be a styrene-based block copolymer. Also, the drug permeation layer may contain the styrene-based block copolymer at a content of 5 to 30% by mass. By this arrangement, permeability, cohesive force, and adhesive strength that are sufficient for a patch can be maintained.

Also, the drug permeation layer may contain a tackifier resin for providing adhesive strength. By this arrangement, the adhesive strength can be reinforced. Also, the drug permeation layer may be a layer with a thickness of 30 to 120 μm. By this arrangement, good adhesion properties can be secured and a drug sufficient for treatment can be controlled in a long-lasting manner.

Also, the polymer that is to be the base of the drug reservoir layer may be a (meth)acrylic-based polymer or a cellulose derivative. Also, the drug reservoir layer may be a non-liquid in a range of 30 to 40° C. Further, the drug may contain bisoprolol or a pharmaceutically allowable salt thereof.

Also, the transdermal preparation may further include a reinforcing layer reinforcing a strength of the drug reservoir layer and disposed at a first principal surface side or the second principal surface side of the drug reservoir layer or inside the drug reservoir layer. By this arrangement, the strength of the drug reservoir layer is reinforced by the reinforcing layer and thus for example when the drug reservoir layer is to be cut by a cutting machine, etc., in a manufacturing process, adhesion or attachment of the drug reservoir layer 2 to a cutting blade is prevented by the presence of the reinforcing layer 8. The transdermal preparation can thus be manufactured with good efficiency.

The reinforcing layer may be polyethylene terephthalate. Also, the reinforcing layer may be a layer of 100 g/m$^2$ to 400 g/m$^2$. Further, the reinforcing layer may be a layer of 150 g/m$^2$ to 350 g/m$^2$.

Advantageous Effects of Invention

By the present invention, skin irritation can be reduced reliably by a simple arrangement in a transdermal preparation containing a drug that is highly irritating to skin.

DESCRIPTION OF EMBODIMENTS

An embodiment of the present invention shall now be described with reference to the attached drawings. In the respective drawings, portions that are the same or are equivalent are provided with the same symbol and redundant description is omitted. Also to facilitate understanding of the description, the drawings are drawn with a portion being enlarged and dimensional proportions do not necessarily match those of the description.

Figure 1:
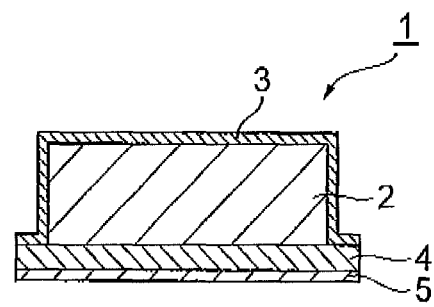
FIG. 1 is a sectional view of a transdermal preparation according to an embodiment.
Figure 2:
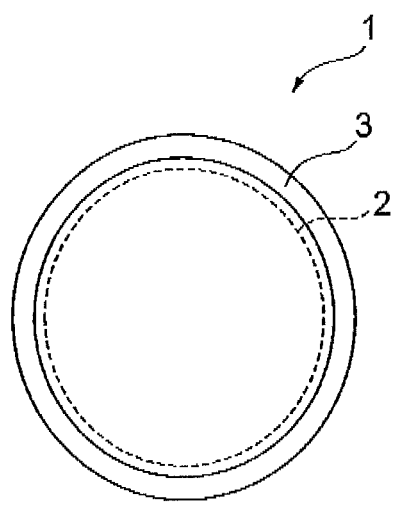
FIG. 2 is a plan view of the transdermal preparation according to the embodiment.

An example of a transdermal preparation, which is one embodiment of the present invention, is shown in FIG. 1 and FIG. 2.

The transdermal preparation 1 according to the present embodiment includes a non-liquid drug reservoir layer 2 containing a drug and a polymer that is to be a base, a drug permeation layer 4, which is lower in permeability of the drug than the drug reservoir layer 2 and is disposed at an upper surface (first principal surface) side that is one surface of the drug reservoir layer 2, and a backing (first backing, second backing) 3 with a bending resistance of 10 to 80 mm that is formed so as to cover a side surface and a lower surface (second principal surface) side of the drug reservoir layer 2. In the present embodiment, in a principal surface of the drug permeation layer 4 not in contact with a release liner 5, portions that do not contact the drug reservoir layer 2 are also covered by the backing 3. Here, the respective layers making up the transdermal preparation 1 are formed into substantially circular shapes.

The drug reservoir layer 2 is a layer that contains the drug and the polymer that is to be the base. The drug reservoir layer 2 is a non-liquid in a range, for example, of 30 to 40° C. Also, an area of the drug reservoir layer 2 may be set to any area in a range of 3 to 150 cm$^2$ in consideration of drug amount and attachment time and an area range of 10 to 100 cm$^2$ is more preferable and an area range of 10 to 50 cm$^2$ is especially preferable. In consideration of ability to contain an amount of the drug that can exhibit a sufficient treatment effect throughout an attachment period of the preparation, ease of manufacture, strength of the preparation, etc., a thickness of the drug reservoir layer 2 is preferably 25 to 1000 μm, more preferably 50 to 500 μm, and even more preferably 100 to 250 μm.

The drug permeation layer 4 is disposed at the skin-contacting side principal surface of the drug reservoir layer 2 and serves a role of preventing the drug reservoir layer 2 from contacting the skin directly. A thickness, material, etc., of the drug permeation layer 4 is not restricted in particular and may be set and selected as suited.

Preferably in consideration of a structure of the preparation and ease of manufacture, the drug permeation layer 4 also has an adhesive property, for example in a range of 30 to 40° C. and functions as a skin adhesion layer as well. That is, the drug permeation layer preferably exhibits a one-second creep compliance greater than $1\times10^{-6}$ cm$^2$/dyne in a range of 30 to 40° C. In such a case, the thickness of the drug permeation layer having the adhesive property is preferably 10 to 200 μm, more preferably 20 to 150 μm, and especially more preferably 30 to 120 μm because the entire preparation can thereby be secured with a good adhesion property with respect to skin throughout the attachment period and be capable of controlling and making a fixed amount of the drug sufficient for treatment be transdermally absorbed in a long-lasting manner.

An area of the drug permeation layer 4 is not restricted in particular as long as it is no less than the area of the drug reservoir layer 2 and is preferably a wider area than that of the drug reservoir layer 2 in order to reliably fix the backing 3 that covers the drug reservoir layer.

Specifically, an outer edge of the drug permeation layer 4 is set preferably in a range of being larger in width by 1 to 10 mm, more preferably in a range of being larger in width by 1 to 7 mm, and even more preferably in a range of being larger in width by 2 to 5 mm than an outer edge of the drug reservoir layer 2. By being larger in width in this range with respect to the outer edge of the drug reservoir layer 2, the backing 3 can reliably cover portions of the upper surface and the side surface of the drug reservoir layer 2 that do not contact the drug permeation layer 4 and also contact the drug permeation layer 4 over a sufficient area to enable maintenance of mechanical strength of the preparation and further facilitate manufacture of the preparation.

A thickness of an entire layer combining the drug reservoir layer 2 and the drug permeation layer 4 is not restricted in particular but is preferably 50 to 1000 µm, more preferably 100 to 500 µm, and especially more preferably 175 to 275 µm. Also, a ratio of the thicknesses of the drug reservoir layer 2 and the drug permeation layer 4 is preferably 1:5 to 5:1 and more preferably 1:1 to 5:1.

As the drug permeation layer 4, that with which the permeability of the drug is lower than that of the drug reservoir layer 2 is used. The drug in the drug reservoir layer 2 is thus adjusted in rate of permeation to skin via the drug permeation layer 4.

Also in the transdermal preparation 1, the backing 3 is not restricted in particular as long as it is drug impermeable and can carry an adhesive layer and, for example, a flexible or non-flexile backing selected from among woven fabrics, knitted fabrics, nonwoven fabrics, polyurethanes, polyesters, polyvinyl acetates, polyvinylidene chlorides, polyethylenes, polyethylene terephthalates, aluminum sheets, etc., composite materials thereof, and laminates thereof may be used. From the point of enabling reduction of skin irritation and drug impermeability to be realized at the same time, a polyethylene terephthalate sheet or a sheet made of a laminate of polyethylene terephthalate and a nonwoven fabric is especially preferable.

Also, the bending resistance of the backing 3 is preferably 10 to 80 mm and more preferably 15 to 70 mm. When the bending resistance of the backing 3 is no more than 10 mm, the backing may be insufficient in strength and may readily tear in an attachment process, etc., and may also have problems of being too soft and being hard to handle due to wrinkling, etc. Also, when the bending resistance is no less than 80 mm, the backing is too hard and tends to be poor in property of following the skin, peel readily and possibly expose the drug reservoir layer, and poor in feeling of use. That is, by setting the bending resistance of the backing 3 to 10 to 80 mm, the transdermal preparation 1 that is safe and excellent in feeling of use can be realized.

The drug reservoir layer 2 of the transdermal preparation 1 contains the polymer, which is to be the base, as the adhesive and is thus high in viscosity, has a suitable viscoelasticity, and thus unlikely to leak liquid as in a reservoir type preparation in which a drug is contained in a liquid component, such as water or alcohol, etc., or in a gel of low viscosity. Thus as long as the mechanical strength of the preparation can be maintained, a thin, soft backing 3 may be used, and there is no need to seal completely by heat sealing, etc. Consequently, not only skin irritation due to the drug but skin irritation due to hardness of the preparation can also be reduced. On the other hand, with a reservoir type preparation, a drug reservoir portion is arranged with the drug being contained in a solvent or low-viscosity gel as mentioned above and thus a backing is required not only to prevent permeation of the drug and the solvent but also to secure a sufficient strength and seal tightly to prevent leakage of liquid. Thus a backing that is thick and heat sealable must be used, and the preparation is thus made hard and poor in the property of following the skin and in the feeling of use.

"Bending resistance" refers to the bending resistance measured under the following conditions by a 45 degree cantilever method defined in JIS L1085. That is, a test piece of 2 cm×15 cm is placed on a horizontal table, with a smooth surface having a 45 degree inclined surface at one end and including a scale on an upper surface, in a manner such that a short side of the test piece is matched with a baseline of the scale, the test piece is gradually slid in the direction of the inclined surface, and the bending resistance is a distance (mm) by which the test piece has been moved when a central point of one short side of the test piece contacts the inclined surface.

Also, the thickness of the backing 3 is normally 1 to 100 µm, preferably 5 to 50 µm, and especially preferably 5 to 25 µm.

By the drug reservoir layer 2 containing the drug and the polymer that is to be the base, the drug permeation layer 4, and the backing 3 with the bending resistance of 10 to 80 mm, the transdermal preparation 1 is provided with the structure with which the drug reservoir layer 2 does not directly contact the skin and thus has characteristics of having a sufficient treatment effect, being low in skin irritation, and also excellent in feeling of use.

The drug reservoir layer 2 of the transdermal preparation 1 contains the polymer. The polymer is not restricted in particular as long as it enables forming of the drug reservoir layer that can hold the drug of the required amount for drug treatment at an amount at which a drug efficacy can be exhibited sufficiently even during administration over a long term and has a suitable viscoelasticity and, for example, a (meth)acrylic-based polymer or a cellulose derivative is preferably used. "(Meth)acrylic" signifies acrylic or methacrylic.

Among (meth)acrylic-based polymers, a (meth)acrylic-based polymer that practically does not have a hydroxyl group in the molecule and has a carboxylic group is preferably used. This is because when a (meth)acrylic-based polymer having a hydroxyl group in the molecule is used, an interaction with bisoprolol (or a salt thereof) occurs and drug stability decreases. Such a (meth)acrylic-based polymer is not restricted in particular as long as it practically does not have a hydroxyl group in the molecule and has a carboxylic group, and 2-ethylhexyl acrylate-vinyl acetate-acrylic acid copolymers, 2-ethylhexyl acrylate-methyl acrylate-glycidyl methacrylate-acrylic acid copolymers, Duro-Tak87-2852, Duro-Tak87-2194, Duro-Tak87-2196, Duro-Tak87-2353, Duro-Tak87-2051, Duro-Tak87-2052, Duro-Tak87-2054, Duro-Tak87-2825, Duro-Tak87-2677 (made by Henkel AG & Co.), etc., can be cited as examples. With the drug reservoir layer 2 using such a carboxylic-group-containing acrylic-based polymer, a drug such as bisoprolol or a pharmaceutically allowable salt thereof can be contained at high concentration and yet with stability.

As examples of the cellulose derivative, hydroxypropyl methylcellulose, methylcellulose, hydroxypropyl cellulose, hypromellose phthalate, hydroxypropyl methylcellulose acetate succinate, etc., can be cited.

The drug that can be contained in the transdermal preparation 1 is not restricted in particular as long as it is a compound that is absorbed via skin and is used for treatment of any of various disorders mentioned below, and nonsteroidal anti-inflammatory analgesics (diclofenac, indomethacin, ketoprofen, felbinac, loxoprofen, ibuprofen, flurbiprofen, tiaprofen, acemetacin, sulindac, etodolac, tolmetin, piroxicam, meloxicam, ampiroxicam, naproxen, azapropazone, methyl salicylate, glycol salicylate, valdecoxib, celecoxib, and rofecoxib), antihypertensive agents (diltiazem, nicardipine, nilvadipine, metoprolol, bisoprolol, and trandolapril), anti-Parkinson agents (pergolide, bromocriptine, ropinirole, and selegiline), bronchodilators (tulobuterol, isoproterenol, and salbutamol), narcotic-based analgesic (fentanyl and morphine), urinary organ agents (oxybutinin), psychoneurotic agents (promazine and chlorpromazine), antidepressants (sertraline, fluoxetine, paroxetine, citalopram, and fluvoxamine), antidementia agents (donepezil, risperidone, rivastigmine, galantamine, and idebenone), expectorants (ambroxol), anti-anxiety drugs (tandospirone), antipsychotic drugs (olanzapine), analeptics (methylphenidate), osteoporosis treatment drugs (raloxifene and alendronate), breast cancer preventing drugs (tamoxifen), anti-obesity drugs (mazindol and sibutramine), anti-insomnia drugs (melatonin), etc., can be cited as examples, and pharmaceutically allowable salts and derivatives thereof may also be used. Although basic drugs among the above readily cause damage of cell membranes of epidermal cells, etc., that are negatively charged and use thereof as transdermal preparations often accompany skin irritation, when such a basic drug is used as the drug of the transdermal preparation that is one embodiment of the present invention, favorable use is made in particular because of the excellent irritation suppression effect.

Also, although a primary skin irritancy of a drug is dependent on a concentration at which the drug contacts the skin and a skin permeation amount, the drug used in the laminated type transdermal preparation 1 according to the present embodiment is preferably a drug that is known to tend to cause skin irritation when a concentration in the preparation is no more than 20% by mass, that is, for example, an antihypertensive agent (diltiazem, nicardipine, nilvadipine, metoprolol, bisoprolol, or trandolapril), an anti-Parkinson agent (pergolide, bromocriptine, ropinirole, or selegiline), an osteoporosis treatment drug (raloxifene or alendronate), an antidepressant (sertraline, fluoxetine, paroxetine, citalopram, or fluvoxamine) or a pharmaceutically allowable salt thereof (hydrochloride, hydrobromide, nitrate, sulfate, phosphate, formate, acetate, trifluoroacetate, propionate, lactate, tartarate, oxalate, fumarate, maleate, citrate, malonate, methanesulfonate, etc.) because the skin irritation can be reduced effectively by the transdermal preparation 1. Among these, bisoprolol or a pharmaceutically allowable salt thereof is especially preferably used.

The content of the drug or pharmaceutically allowable salt thereof that is contained in the drug reservoir layer 2 is normally 1 to 60% by mass, preferably 20 to 50% by mass, and especially preferably 30 to 50% by mass. The drug may be contained in the drug reservoir layer 2 in a dissolved state, supersaturated crystalline state, or dispersed state. A content of no more than 1% by mass may not be preferable in some cases because sufficient skin permeation cannot be obtained, and a content of no less than 60% by mass is not preferable because an adequate cohesive force cannot be maintained as a patch.

The drug reservoir layer 2 may furthermore contain at least one of either a solubilizer or an absorption enhancer. The solubilizer may be any compound that exhibits a dissolving action on the drug. Also, the absorption enhancer may be any compound that is conventionally known to exhibit an absorption enhancing effect on skin. As examples of at least one of either the solubilizer or the absorption enhancer, fatty acids, fatty alcohols, fatty acid esters, and amides with 6 to 20 carbon chains, ethers, aromatic organic acids, aromatic alcohols, and aromatic organic acid esters and ethers (the above may be either saturated or unsaturated or may be either cyclic, linear, or branched) as well as lactic acid esters, acetic acid esters, monoterpene-based compounds, sesquiterpene-based compounds, azones, azone derivatives, pyrrothiodecane, glycerin fatty acid esters, propylene glycol fatty acid esters, sorbitan fatty acid esters (Span type), polysorbates (Tween type), polyethylene glycol fatty acid esters, polyoxyethylene hardened castor oils (HCO type), polyoxyethylene alkyl ethers, sucrose fatty acid esters, vegetable oils, etc., can be cited.

Specifically, lauryl alcohol, myristyl alcohol, oleyl alcohol, isostearyl alcohol, diethyl sebacate, glycerol monocaprate, glycerol monolaurate, glycerol monooleate, sorbitan monolaurate, propylene glycol monolaurate, polyoxyethylene lauryl ether, and pyrrothiodecane are preferable, and isopropyl myristate is more preferable.

One type of the solubilizer or absorption enhancer may be used solitarily or two or more types may be used in combination. Although the contained amount thereof is not restricted in particular, the contained amount on a basis of the entire amount of compounds contained in the drug reservoir layer 2 is preferably 1 to 40% by mass, more preferably 1 to 20% by mass, and especially preferably 1 to 10% by mass.

The base of the drug permeation layer 4 includes a rubber-based adhesive component. As the rubber-based adhesive component, polyisobutylene, isoprene rubber, a styrene-based block copolymer, such as styrene-isoprene-styrene block copolymer or styrene-butadiene-styrene copolymer, etc., styrene-butadiene rubber, polysiloxane, etc., may be used favorably, and one type of such compound may be used solitarily or several types may be used in combination. From the points of adhesive property and being capable of controlling the release of the drug in a long-lasting manner, styrene-isoprene-styrene block copolymer or polyisobutylene is used especially favorably.

In regard to the content of the styrene-isoprene-styrene block copolymer in the drug permeation layer 4, sufficient permeability and cohesive force as a patch tend not to be maintained when the content is no more than 5% by mass, a sufficient adhesive strength as a patch cannot be maintained when the content is no less than 30% by mass, and thus 5 to 30% by mass is preferable.

Also with the drug permeation layer 4, it is further preferable for two or more types of polyisobutylenes of different molecular weights to be used in combination with the styrene-isoprene-styrene block copolymer. The content of the synthetic rubber is preferably 1 to 30% by mass and more preferably 5 to 20% by mass.

Although there may be a case where the drug permeation layer 4 and the drug reservoir layer 2 contain the same polymers, the other components are blended so that the drug permeability of the drug permeation layer 4 is less than the drug permeability of the drug reservoir layer 2.

It is further preferable for the drug permeation layer 4 to contain a tackifier resin in a case where an adhesive strength that is applicable for at least 12 hours is insufficient, and rosin derivatives (for example, rosin, rosin glycerol ester, hydrogenated rosin, hydrogenated rosin glycerol ester, rosin pentaerythritol ester, etc.), alicyclic saturated hydrocarbon resins (for example, Arkon P-100, made by Arakawa Chemical Industries, Ltd.), aliphatic hydrocarbon resins (for example, Quintone B170, made by Zeon Corp.), terpene resins (for example, Clearon P-125, made by Yasuhara Chemical Co., Ltd.), maleic acid resins, etc., can be cited as examples of the tackifier resin that can be used. Among these, a hydrogenated rosin glycerol ester, alicyclic saturated hydrocarbon resin, or terpene resin is preferable, and an alicyclic saturated hydrocarbon resin is especially preferable.

One type of the tackifier agent may be used solitarily or two or more types may be used in combination. Although the contained amount thereof is not restricted in particular, the contained amount is preferably 10 to 60% by weight, more preferably 20 to 60% by weight, and especially preferably 30 to 50% by weight.

Also, the drug permeation layer 4 may contain a plasticizer. Petroleum-based oils (for example, paraffinic process oils, naphthenic process oils, and aromatic process oils), squalane, squalene, vegetable oils (for example, olive oil, camellia oil, castor oil, tall oil, and peanut oil), silicone oils, dibasic acid esters (for example, dibutyl phthalate, dioctyl phthalate, etc.), liquid rubber (for example, polybutene and liquid isoprene rubbers), liquid fatty acid esters (isopropyl myristate, hexyl laurate, diethyl sebacate, and isopropyl sebacate), diethylene glycol, polyethylene glycols, glycol salicylate, propylene glycol, dipropylene glycol, triacetin, triethyl citrate, crotamiton, etc., can be cited as examples of the plasticizer. Liquid paraffins, liquid polybutene, isopropyl myristate, diethyl sebacate, and hexyl laurate are especially preferable.

One type of the plasticizer may be used solitarily or two or more types may be used in combination. Although the contained amount of the plasticizer is not restricted in particular, the contained amount in the drug permeation layer is preferably 5 to 50% by weight, more preferably 10 to 40% by weight, and especially preferably 20 to 30% by weight.

Further, an antioxidant, filler, crosslinking agent, preservative, UV absorber, etc., may be contained as necessary in the drug reservoir layer 2 and the drug permeation layer 4.

Tocopherols and ester derivatives thereof, ascorbic acid, ascorbic acid stearic acid ester, nordihydroguaiaretic acid, dibutylhydroxytoluene (BHT) and butylhydroxyanisole are preferable as the antioxidant, calcium carbonate, magnesium carbonate, silicates (for example, aluminum silicate, magnesium silicate, etc.), silicic acid, barium sulfate, calcium sulfate, calcium zincate, zinc oxide, and titanium dioxide are preferable as the filler, and thermoset resins, such as amino resins, phenol resins, epoxy resins, alkyd resins, unsaturated polyesters, etc., isocyanate compounds, blocked isocyanate compounds, organic crosslinking agents, and inorganic crosslinking agents, such as metals and metallic compounds. etc., are preferable as the crosslinking agent. Also, ethyl parahydroxybenzoate, propyl parahydroxybenzoate, and butyl parahydroxybenzoate are preferable as the preservative, and p-aminobenzoic acid derivatives, anthranilic acid derivatives, salicylic acid derivatives, coumarin derivatives, amino-acid-based compounds, imidazoline derivatives, pyrimidine derivatives, and dioxane derivatives are preferable as the UV absorber.

Although the contained amount of each of the antioxidant, filler, crosslinking agent, preservative, and UV absorber is not restricted in particular, the total amount of the antioxidant, filler, crosslinking agent, preservative, and UV absorber as the content in each of the drug reservoir layer and drug permeation layer individually and on the basis of the total amount of components contained in each layer is preferably 0.01 to 20% by weight, more preferably 0.1 to 10% by weight, and especially preferably 0.1 to 5% by weight.

A further adhesive layer of, for example, an acrylic adhesive, rubber-based adhesive, or silicone adhesive may be disposed between the drug reservoir layer 2 and the drug permeation layer 4 of the transdermal preparation 1 or on the skin contacting side surface of the drug permeation layer 4.

Figure 8:
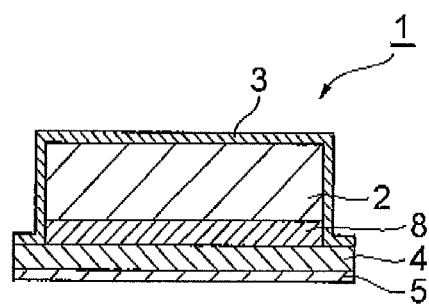
FIG. 8 is a sectional view of a modification example of a transdermal preparation.

Also as shown in FIG. 8, a reinforcing layer 8 may be interposed between the drug reservoir layer 2 and the drug permeation layer 4 as long as the permeation of the drug is not obstructed. Further, the reinforcing layer 8 suffices to be disposed between a portion of the backing 3 formed on the principal surface side of the drug reservoir layer 2 and the drug permeation layer 4 and may be present inside the drug reservoir layer 2. That is, the reinforcing layer 8 is formed on an upper surface side or a lower surface side of the drug reservoir layer 2 or inside the drug reservoir layer 2. Especially in a case where cutting of the drug reservoir layer 2 by a cutter is required in a manufacturing process of the transdermal preparation 1, the reinforcing layer 8 reinforces a strength of the drug reservoir layer 2 and the presence of the reinforcing layer 8 thus prevents adhesion or attachment of the drug reservoir layer 2 to the cutter and can simplify the manufacturing process. Also, a handling property is improved because the reinforcing layer 8 imparts a suitable strength to the transdermal preparation 1.

From standpoints of increasing the mechanical strength during cutting of the drug reservoir layer 2, preventing the adhesion of the drug reservoir layer 2 to the cutter, and not obstructing the permeation of the drug, the thickness of the reinforcing layer 8 is required to be 20 μm to 250 μm and is preferably 50 μm to 200 μm. The bending resistance is required to be 5 mm to 150 mm and is preferably 10 mm to 100 mm. Further a weight per unit area (specific weight per unit area in a case of a textile) is required to be 100 $g/m^2$ to 400 $g/m^2$ and is preferably 150 $g/m^2$ to 350 $g/m^2$.

Films made of such components as polyurethane, polyester (polyethylene terephthalate, etc.), polypropylene, polyvinyl acetate, ethylene-vinyl acetate copolymer, polyvinylidene chloride, polyethylene, nylon, acryl, cotton, rayon, etc., and textile sheets, such as woven fabrics, nonwoven fabrics, meshes, etc., can be cited as examples of the reinforcing layer 8. Among the above, polyester is preferable as a component, and a polyester mesh of mesh form is especially preferable.

The adhesive layer of the patch of the transdermal preparation 1 preferably includes the release liner 5 on the surface that contacts the skin at the opposite side of the backing 3. Films of polyester, such as polyethylene terephthalate, films of polyvinyl chloride, polyvinylidene chloride, etc., laminated films of quality paper and a polyolefin, etc., can be cited as examples of the release liner. As such a release liner 5, that having a silicone treatment applied to the surface at the side that contacts the adhesive layer is preferable. By the silicone treatment, the release liner 5 can be peeled off readily from the adhesive layer for use. The release liner 5 having a thickness of 50 to 150 μm can be used favorably.

The above-described embodiment illustrates one example of the transdermal preparation according to the present invention. The transdermal preparation according to the present invention is not restricted to the transdermal preparation according to the embodiment, and the transdermal preparation 1 according to the embodiment may be modified or applied to other objects within a range not falling outside the gist of the claims.

Figure 9:
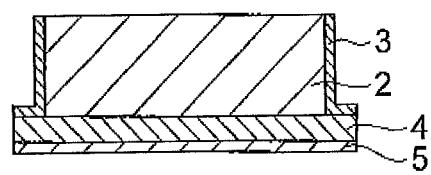
FIG. 9 is a sectional view of a modification example of a transdermal preparation.

For example, although with the above embodiment, an example of arranging the backing 3 to cover the side surface and the lower surface of the drug reservoir layer 2 was described, the backing 3 may instead be formed just at the side surface of the drug reservoir layer 2 as in a transdermal preparation shown in FIG. 9. Even when the backing is formed in this manner, direct contact of the drug reservoir layer 2 with the skin can be avoided during actual use.

Figure 10:
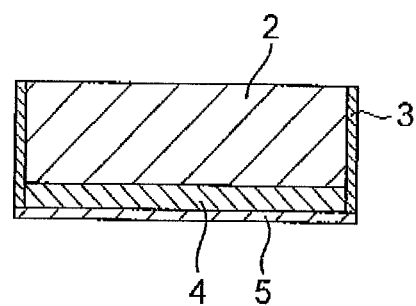
FIG. 10 is a sectional view of a modification example of a transdermal preparation.

Also, although with the above embodiment, an example was described where, in the principal surface of the drug permeation layer 4 not in contact with the release liner 5, the portion that does not contact the drug reservoir layer 2 is also covered by the backing 3, the portion that does not contact the drug reservoir layer 2 does not have to be covered by the backing 3. Further, the backing 3 may be formed on the side surfaces of the drug reservoir layer 2 and the drug permeation layer 4 as in a transdermal preparation shown in FIG. 10.

Figure 11:
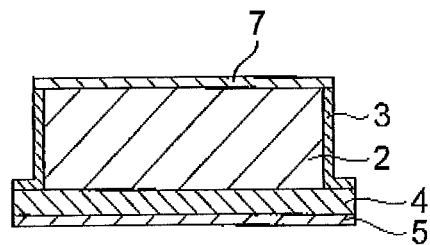
FIG. 11 is a sectional view of a modification example of a transdermal preparation.

Also, although with the above embodiment, an example of the arranging the backing 3 to cover the side surface and the lower surface of the drug reservoir layer 2 was described, the backing 3 may cover just the side surface of the drug reservoir layer 2 and a backing (second backing) 7, made of a different material from that of the backing 3, may cover the lower surface of the drug reservoir layer 2 as shown in FIG. 11. The material of the backing that covers the lower surface of the drug reservoir layer 2 may be selected as suited from among the materials of the backing 3 described with the embodiment above.

Figure 12:
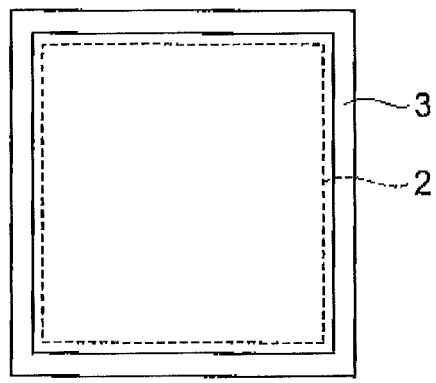
FIG. 12 is a top view of a modification example of a transdermal preparation.

Also, although with the above embodiment, an example where the respective layers of the transdermal preparation 1 are substantially circular was described, the layers may be formed to rectangular forms as shown in FIG. 12.

Also, although with the above embodiment, an example where the drug permeation layer 4 has an adhesive property was described, in a case where a further adhesive layer of, for example, an acrylic adhesive, rubber-based adhesive, or silicone adhesive is disposed on the skin contacting side surface of the drug permeation layer 4 or a case where the transdermal preparation 1 is adhered by a bandage, the drug permeation layer 4 does not have to have an adhesive property.

EXAMPLES

Although the present invention shall now be described in further detail below by way of examples, the present invention is not restricted to the following examples.
(Formulation of preparations) Drug reservoir layers of transdermal preparations (bisoprolol-containing preparations) of Examples 1 to 3 and Comparative Example 1 have the following composition.
(Drug Reservoir Layer)
Acrylic adhesive (—COOH type) . . . 50%
Liquid paraffin . . . 10%
Bisoprolol . . . 40%
Also, drug reservoir layers of transdermal preparations (bisoprolol-containing preparations) of Example 4 and Comparative Example 2 have the following composition.
(Drug Reservoir Layer)
Cellulose derivative . . . 60%
Bisoprolol . . . 40%
Also, drug permeation layers of the transdermal preparations of Examples 1 to 4 and Comparative Examples 1 and 2 have the following composition.
(Drug Permeation Layer)
Styrene-isoprene-styrene block copolymer . . . 20%
Low molecular weight polyisobutylene . . . 5%
High molecular weight polyisobutylene . . . 13%
Alicyclic saturated hydrocarbon resin . . . 40%
Liquid paraffin . . . 22%

Example 1

Figure 3:
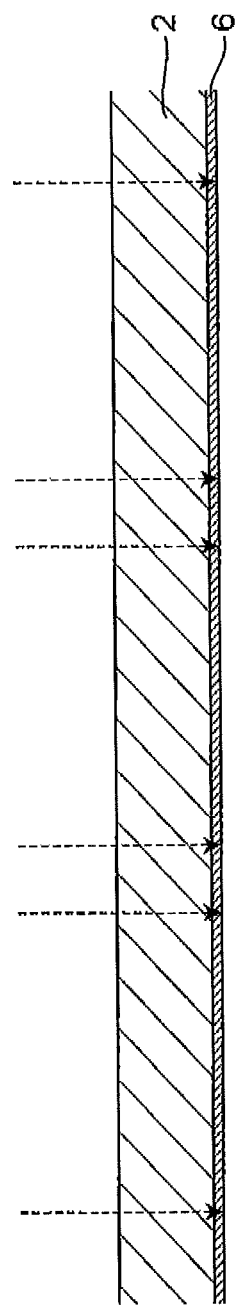
FIG. 3 is a schematic view of a manufacturing process of the transdermal preparation according to the embodiment.

(Method for manufacturing transdermal preparations each of which is one embodiment of the present invention) A coating solution was obtained by mixing bisoprolol in a solution having a 2-ethylhexyl acrylate-butyl acrylate-acrylic acid copolymer dissolved in ethyl acetate, toluene, and hexane and having a liquid paraffin dispersed therein. After coating the coating solution obtained onto a polyethylene terephthalate mold release film 6, the solvent was removed by drying to form an adhesive layer having a predetermined plaster thickness (200 μm) and a drug reservoir layer 2 of a transdermal preparation that is one embodiment of the present invention was thereby obtained (FIG. 3). The contained proportions of the respective components were set as indicated in the formulation above.

Meanwhile, a coating solution, in which a styrene-isoprene-styrene block copolymer [SIS], a polyisobutylene [PIB] (high molecular weight), a polyisobutylene [PIB] (low molecular weight), an alicyclic saturated hydrocarbon resin, and a liquid paraffin were dissolved in toluene, was coated onto a polyethylene terephthalate mold release film 6 and the solvent was thereafter removed by drying to form a drug permeation layer 4 having a predetermined plaster thickness (50 μm). The contained proportions of the respective components were set as indicated in the formulation above.

Figure 4:
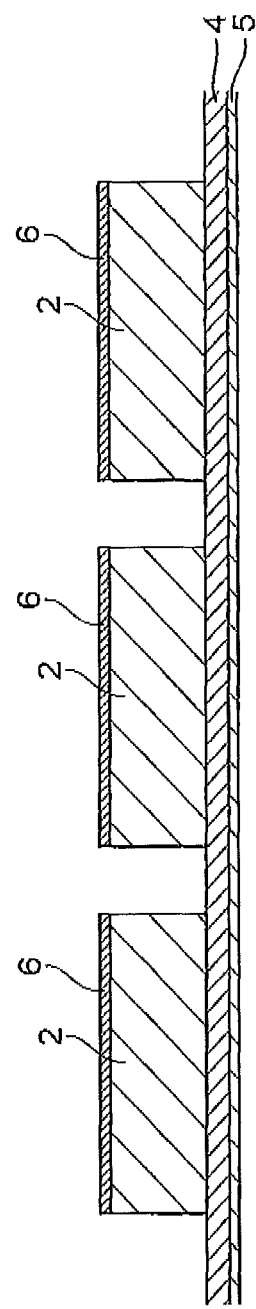
FIG. 4 is a schematic view of the manufacturing process of the transdermal preparation according to the embodiment.
Figure 5:
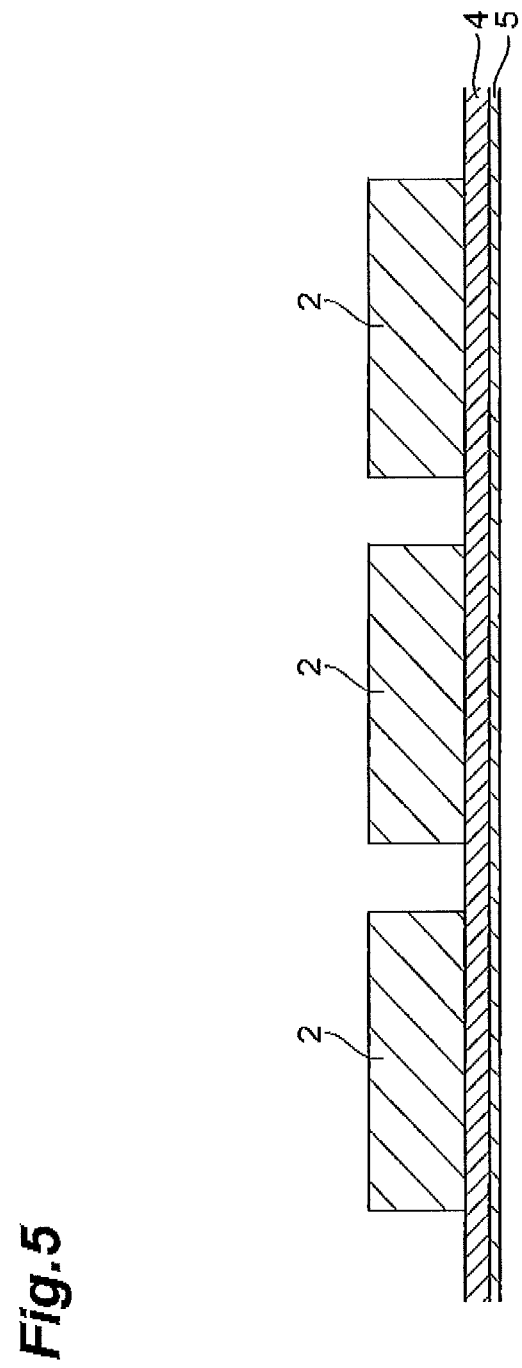
FIG. 5 is a schematic view of the manufacturing process of the transdermal preparation according to the embodiment.
Figure 6:
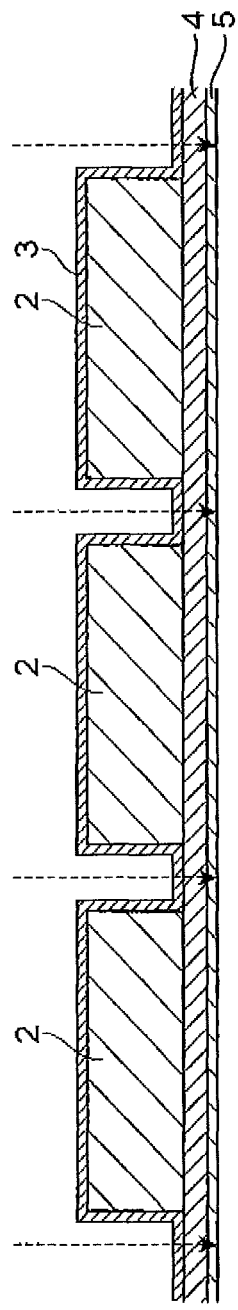
FIG. 6 is a schematic view of the manufacturing process of the transdermal preparation according to the embodiment.
Figure 7:
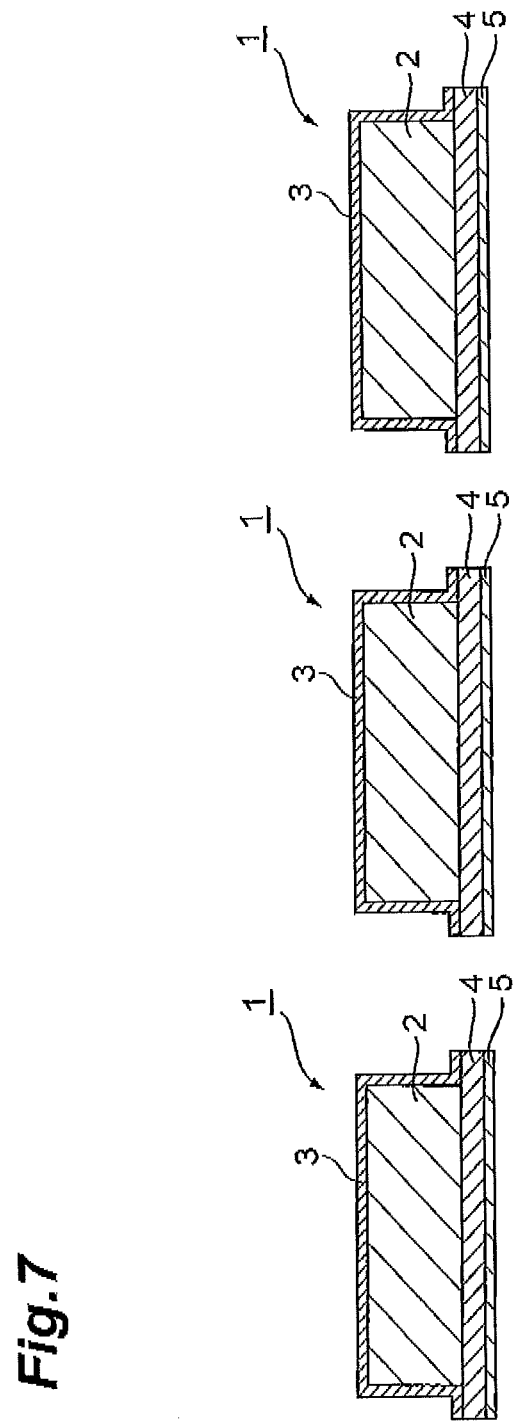
FIG. 7 is a schematic view of the manufacturing process of the transdermal preparation according to the embodiment.

Both principal surfaces of each of the priorly obtained drug reservoir layer 2 and drug permeation layer 4 were protected by release liners. The drug reservoir layer 2 was then punched out to portions of arbitrary size (FIG. 3), the release liner at one surface of the drug reservoir layer 2 was peeled off, likewise the release liner 5 at one surface of the drug permeation layer 4 was peeled off, and the principal surface of the drug reservoir layer 2 from which the release liner was peeled off and the principal surface of the drug permeation layer 4 from which the release liner 5 was peeled off were adhered together (FIG. 4). The remaining release liner and the polyethylene terephthalate mold release film 6 were then peeled off from the other principal surface of the drug reservoir layer 2 (FIG. 5) and a backing 3 was adhered onto the surface and then punched out to portions of the size of the preparation (FIG. 6) to obtain the transdermal preparations, each of which one embodiment of the present invention (FIG. 7). The backing 3 that was used was made of polyethylene terephthalate (bending resistance: 47 mm, thickness: 25 μm).

Examples 2 and 3

(Method for manufacturing transdermal preparations each of which is one embodiment of the present invention) Before protecting the principal surfaces of the drug reservoir layer 2 with the release liners, a reinforcing layer 8 was formed at one principal surface side of the drug reservoir layer 2. After then protecting with the release liners, the drug reservoir layer 2 was punched out to portions of arbitrary size from the reinforcing layer 8 side, the release liner at the reinforcing layer 8 side was peeled off, the release liner 5 of the drug permeation layer 4 was peeled off from just one surface, and the principal surface of the reinforcing layer 8 and the principal surface of the drug permeation layer 4 from which the release layer 5 was peeled off were adhered together. Besides the above, the manufacturing method is the same as that of Example 1.

Example 4

(Method for manufacturing transdermal preparations each of which is one embodiment of the present invention) After adding ethanol to dissolve a cellulose derivative, bisoprolol was added, and sufficient stirring was performed to obtain a coating solution. After then coating the coating solution obtained onto a polyethylene terephthalate mold release film, the ethanol, which is the solvent, was removed by drying to form a drug reservoir layer. The layer was adjusted to a predetermined plaster thickness (200 μm) and further adhered to a polyethylene terephthalate backing to obtain the drug reservoir layer 2 of a transdermal preparation that is one embodiment of the present invention (FIG. 3). The contained proportions of the respective components were set as indicated in the formulation above. Besides this, the manufacturing method is the same as that of Example 1.

Methods for manufacturing the transdermal preparations, each of which is one embodiment of the present invention, were described as examples in Examples 1 to 4, and the drug reservoir layer 2 and the drug permeation layer 4 can be manufactured readily at low cost because, as mentioned above, both contain polymers, are thus high in viscosity, have viscoelasticity, and thus do not require complete sealing of a liquid component by a backing, a release controlling film, and the drug permeation layer 4 as in a reservoir type preparation. Also, an adhesion tab that is a joining portion of the backing 3 and the drug permeation layer 4 can be arranged as a minimal portion because the viscosity of the drug reservoir layer 4 is high. The transdermal preparation can thereby be made compact. Further, a large number of transdermal preparations can be manufactured from the drug reservoir layer 2 shown in FIG. 3 because the size of one transdermal preparation can be made small. However, the method for manufacturing the transdermal preparation that is one embodiment of the present invention is not restricted to the methods described above.

Comparative Example 1

(Manufacturing method of Comparative Example 1) A coating solution was obtained by mixing bisoprolol in a solution having a 2-ethylhexyl acrylate-butyl acrylate-acrylic acid copolymer dissolved in ethyl acetate, toluene, and hexane and having a liquid paraffin dispersed therein. After coating the coating solution obtained onto a polyethylene terephthalate mold release film, the solvent was removed by drying to form an adhesive layer having a predetermined plaster thickness (200 μm). The layer was adhered to a polyethylene terephthalate backing (bending resistance: 47 mm, thickness: 25 μm) and a drug reservoir layer of a transdermal preparation was thereby obtained.

Meanwhile, a coating solution, in which a styrene-isoprene-styrene block copolymer, a polyisobutylene (high molecular weight), a polyisobutylene (low molecular weight), an alicyclic saturated hydrocarbon resin, and a liquid paraffin were dissolved in toluene, was coated onto a polyethylene terephthalate mold release film and the solvent was thereafter removed by drying to form a drug permeation layer having a predetermined plaster thickness (50 μm). Lastly, the polyethylene terephthalate mold release film was peeled off from the priorly obtained drug reservoir layer, the adhesive layers were adhered together, and punching out to portions of predetermined size was performed to obtain transdermal preparations of Comparative Example 1 with which a side surface of the drug reservoir layer is not covered. The contained proportions of the respective components were set as indicated in the formulation above.

Comparative Example 2

(Manufacturing method of Comparative Example 2) A drug reservoir layer was manufactured in the same manner as in Example 4. The contained proportions of the respective components were set as indicated in the formulation above. Besides this, the manufacturing method is the same as that of Comparative Example 1.

Test Example 1

(Skin irritation test) (Rabbit skin primary irritation test) A 2 cm×2 cm test substance was adhered onto a skin of a shaved back portion of a rabbit and fixed from above by a Serapoa (registered trademark) tape (3.8 cm×5 cm, Nichiban Co., Ltd.), and after putting on a rabbit jacket (1410120: Lomir Biomedical Inc.), the rabbit was returned to a cage. 24 hours after adhesion, the test substance was peeled off, naked eye observation regarding erythema/crust and edema formation was performed 1 hour, 24 hours, and 48 hours after peeling and scoring was performed based on evaluation standards of Draize et al (table below).

The judgment of skin primary irritation was performed by computing a primary irritation index (P.I.I.). An average score regarding erythema and edema formation at 1 hour, 24 hours, and 48 hours after peeling was determined for each individual and an average score total was determined for each group and divided by 3 to compute the primary irritation index.

(Skin Irritation Test Results)

TABLE 1

|  | Comparative Example 1 | Example 1 |
| --- | --- | --- |
| Preparation portion | 0.5 | 0.6 |
| Outer peripheral (edge) portion | 1.8 | 1.0 |

As shown in Table 1, unlike the results of Comparative Example 1, the transdermal preparation that is one embodiment of the present invention (Example 1) is significantly decreased in skin irritation at the peripheral portion of the preparation and the effect of the present invention was thus verified.

TABLE 2

|  | Comparative Example 2 | Example 4 |
| --- | --- | --- |
| Preparation portion | 0.8 | 1.0 |
| Outer peripheral (edge) portion | 0.4 | 0.0 |

As shown in Table 2, unlike the result of Comparative Example 2, the transdermal preparation that is one embodiment of the present invention (Example 4) is significantly decreased in skin irritation at the peripheral portion of the preparation and the effect of the present invention was thus verified.

As described above, with Test Example 1, in both the case of employing a (meth)acrylic-based polymer in the drug reservoir layer and the case of employing a cellulose derivative in the drug reservoir layer, the skin irritation decreased significantly at the peripheral portion of the preparation and the effect of the present invention was thus verified.

Test Example 2

(Yield test) A yield by a process simulating automated manufacture was evaluated. The drug reservoir layer 2 (without the reinforcing layer 8), which was described in the manufacturing process of Example 1 and with which both principal surfaces are protected by the release liners, and the drug reservoir layers 2 (with the reinforcing layers 8), which were described in the manufacturing process of Examples 2 and 3 and with which both principal surfaces are protected by the release liners, were used. With Examples 2 and 3, the reinforcing layers 8 described in Table 2 below were provided. The release liner at one principal surface of the drug reservoir layer 2 of Example 1 and the release liners at the reinforcing layer 8 sides of the drug reservoir layers 2 of Examples 2 and 3 were respectively peeled off and half-cuts were made from those surfaces by a cutting blade to form arbitrary shapes. Half-cut products that could be counted as non-defective products (those with good appearance befitting of a finished product) after peeling off unnecessary portions as edge scraps were then counted and a proportion with respect to the number cut was computed as a yield. Also, whether or not the drug reservoir layer 2 became attached to the cutting blade was checked visually.

TABLE 3

| Reinforcing layer | Yield (%) | Attachment of adhesive body to cutting blade |
| --- | --- | --- |
| None (Example 1) | Low (0 to 29) | Yes |
| Polyvinyl acetate film (Example 2) | Medium (30 to 59) | Yes |
| Polyester mesh (Example 3) | High (60 to 100) | No |

As shown in Table 3, in comparison to the case where the reinforcing layer 8 was not provided (Example 1), the yield increased in the cases where the reinforcing layer 8 was provided (Examples 2 and 3). In particular, when the polyester mesh reinforcing layer 8 (Example 3) was used, the yield took on a high value (60 to 100%). Also when the reinforcing layer 8 was made a polyester mesh (Example 3), attachment of the adhesive body to the cutting blade was not observed. It was thus confirmed that by providing the reinforcing layer 8, manufacture is facilitated and improvement of yield can be anticipated for automated manufacture.

Test Example 3

Figure 13:
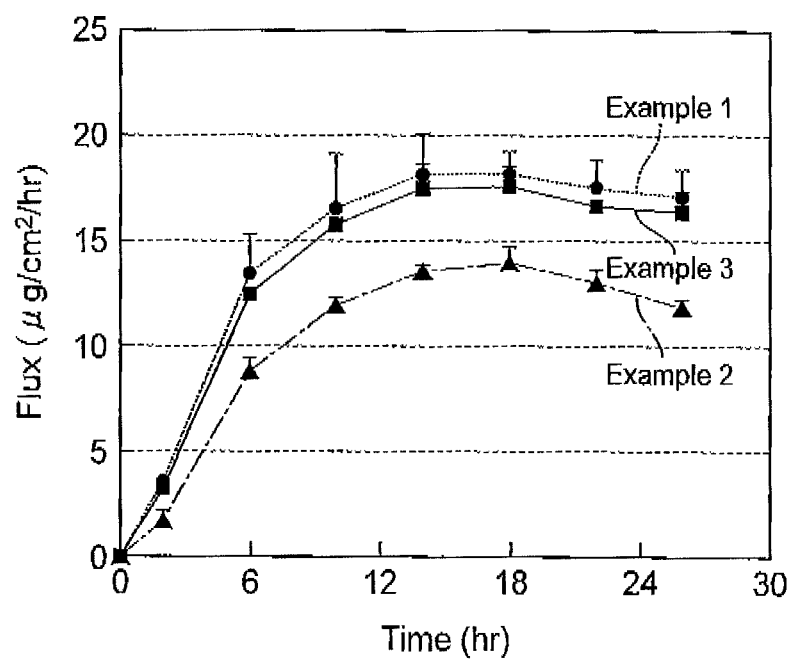
FIG. 13 is a graph of results of a skin permeation test.

(Hairless mouse skin permeation test) Skin exfoliated from a back portion of a hairless mouse (female, 8 weeks old) was attached to a flow-through cell, in which warm water of 32° C. was circulated, with a dermis side set at a receptor tank side, and a patch indicated in Table 2 was adhered to a keratinous layer side of the skin. PBS was then used as a receptor solution and made to flow at a rate of 3.75 ml/H, and the receptor solution was sampled every 4 hours. Along with measuring the flow rate of the receptor solution, a drug concentration in the sampled receptor solution was measured using high-performance liquid chromatography. From the obtained flow rate and the measurement values of the drug concentration, a drug permeation rate per hour was computed and a drug permeation rate per unit area of skin (flux) was determined. The results are shown in FIG. 13. As shown in FIG. 13, the patch of Example 3 that is provided with the reinforcing layer 8 (solid line) exhibited a flux equivalent to that of the patch of Example 1 that is not provided with the reinforcing layer 8, showing that the polyester mesh reinforcing layer 8 does not obstruct the permeability of the drug.

INDUSTRIAL APPLICABILITY

The transdermal preparation, which is one embodiment of the present invention, enables a drug, such as bisoprolol which exhibits skin irritation when put in contact with skin at a high concentration, to be transdermally administered reliably and persistently at a fixed amount necessary for treatment and is also sufficiently decreased in skin irritation. It is thus safe, excellent in feeling of use, capable of being manufactured easily at low cost, and thus industrially useful.

REFERENCE SIGNS LIST

1 . . . transdermal preparation, 2 . . . drug reservoir layer, 3 . . . backing (first backing, second backing), 4 . . . release liner, 8 . . . reinforcing layer.

The invention claimed is:

1. A transdermal preparation, comprising:
   a non-liquid drug reservoir layer having first and second principal surfaces, and comprising a drug and a polymer that is to be a base;
   a drug permeation layer disposed at the first principal surface of the drug reservoir layer and being lower in permeability of the drug than the drug reservoir layer; and
   a first backing with a bending resistance of 10 to 80 mm that is formed so as to cover a side surface of the drug reservoir layer;
   wherein the drug reservoir layer contains a (meth)acrylic-based polymer or a cellulose derivative, and
   the drug permeation layer contains a tackifier resin and a styrene-based block copolymer, and
   the drug comprises bisoprolol and the drug is configured to be adjusted in rate of permeation to skin via the drug permeation layer.

2. The transdermal preparation according to claim 1, further comprising: a second backing formed so as to cover the second principal surface of the drug reservoir layer.

3. The transdermal preparation according to claim 2, wherein the second backing is formed integral with the first backing.

4. The transdermal preparation according to claim 1, wherein the first backing is a polyethylene terephthalate film or a sheet made of a laminate of polyethylene terephthalate and a nonwoven fabric.

5. The transdermal preparation according to claim 1, wherein the drug permeation layer has a wider area than the drug reservoir layer.

6. The transdermal preparation according to claim 1, wherein the drug permeation layer exhibits a one-second creep compliance greater than $1 \times 10^{-6}$ cm$^2$/dyne in a range of 30 to 40° C.

7. The transdermal preparation according to claim 1, wherein the drug permeation layer has a thickness of from 30 to 120 μm.

8. The transdermal preparation according to claim 1, wherein the drug permeation layer comprises the styrene-based block copolymer at a content of 5 to 30% by mass.

9. The transdermal preparation according to claim 1, wherein the drug reservoir layer has a thickness of from 100 to 250 μm.

10. The transdermal preparation according to claim 1, wherein the drug reservoir layer is a non-liquid at a temperature in a range of from 30 to 40° C.

11. The transdermal preparation according to claim 1, further comprising: a reinforcing layer reinforcing a strength of the drug reservoir layer and disposed at the first principal surface or the second principal surface of the drug reservoir layer or in the drug reservoir layer.

12. The transdermal preparation according to claim 11, wherein the reinforcing layer is polyethylene terephthalate.

13. The transdermal preparation according to claim 11, wherein the reinforcing layer is a layer of 100 $g/m^2$ to 400 $g/m^2$.

14. The transdermal preparation according to claim 11, wherein the reinforcing layer is a layer of 150 $g/m^2$ to 350 $g/m^2$.

\* \* \* \* \*